United States Patent [19]

Kawahara et al.

[11] 4,164,506
[45] Aug. 14, 1979

[54] PROCESS FOR PRODUCING LOWER ALCOHOL ESTERS OF FATTY ACIDS

[75] Inventors: Yoshiharu Kawahara, Osaka; Toshio Ono, Wakayama, both of Japan

[73] Assignee: Kao Soap Co., Ltd., Tokyo, Japan

[21] Appl. No.: 884,835

[22] Filed: Mar. 9, 1978

[30] Foreign Application Priority Data

Mar. 17, 1977 [JP] Japan .................................. 52-29709

[51] Int. Cl.$^2$ .......................... C11C 3/02; C09F 5/08
[52] U.S. Cl. .............................. 260/410.9 R; 260/410; 260/421
[58] Field of Search ......... 260/410, 410.9 R, 410.9 E, 260/421

[56] References Cited

U.S. PATENT DOCUMENTS

| | | | |
|---|---|---|---|
| 2,290,609 | 7/1942 | Goss | 260/410.9 E |
| 2,383,596 | 8/1945 | Dreger | 260/410.9 E |
| 2,383,601 | 8/1945 | Keim | 260/410.9 E |

*Primary Examiner*—John F. Niebling
*Attorney, Agent, or Firm*—Blanchard, Flynn, Thiel, Boutell & Tanis

[57] ABSTRACT

Lower alcohol esters of fatty acids are produced by esterifying free fatty acids of unrefined fats with a lower alcohol in an amount larger than its solubility in the fats in the presence an acid catalyst; separating the product mixture into the fat layer and the lower alcohol layer, so that the latter may be removed out; and then effecting the interesterification reaction between the resulting, refined fats and a lower alcohol with an alkali catalyst.

13 Claims, No Drawings

PROCESS FOR PRODUCING LOWER ALCOHOL ESTERS OF FATTY ACIDS

BACKGROUND OF THE INVENTION

1. FIELD OF THE INVENTION

This invention relates to a process for producing lower alcohol esters of fatty acids. More particularly, the present invention relates to an improved process for producing lower alcohol esters of fatty acids from unrefined fats which contain impurities, such as polypeptides and phospholipids in addition to free fatty acids, by the interesterification method.

2. DESCRIPTION OF THE PRIOR ART

Lower alcohol esters of fatty acids have many applications. For example, they are used as a raw material for the production of higher alcohols by means of catalytic hydrogenation, and various surface active agents. They are generally produced either by interesterification between fats and lower alcohols or by esterification in which the fatty acids obtained by hydrolysis of the fats are esterified with a lower alcohol. On the industrial scale, however, the interesterification method has generally been employed between fats and lower alcohols in the presence of an alkali catalyst.

It is usual that unrefined fats contain about 2 to 5% of free fatty acids and impurities such as polypeptides, and phospholipids, although this depends on the kind of fat that is used. If such unrefined fats are used as a raw material for the interesterification reaction as they are, the alkali catalyst is consumed also by the free fatty acids contained therein. Unless a larger amount of the alkali is used, the interesterification reaction does not proceed with ease. Furthermore, due to the emulsifying and solubilizing action of the resulting soap of the fatty acids, a greater amount of the fats are dissolved in the glycerol layer during the interesterification. It causes such problems as deterioration of the qualities of the ester and glycerol, and increase in the loss of the materials, and so forth.

To solve these problems, various methods have been applied to the interesterification reaction between fats and lower alcohols using an alkali catalyst at a relatively low temperature not higher than 100° C. For example, a preparative refining step is incorporated before the interesterification step to remove impurities such as free fatty acids from the reaction system, as illustrated in the following methods (1) through (3), and other specific treating steps are incorporated, as illustrated in the following methods (4) and (5).

(1) Alkali refining method:

An alkali such as caustic soda is added to change the free fatty acids to fatty acid soaps, and these are removed by washing. (described, for example, in Yushi Kagaku (Fat Chemistry)", Iwanami Zensho).

(2) Solvent extraction method:

Utilizing the solubility difference in a solvent (e.g. methanol) between the fatty acid and the triglyceride, the free fatty acid is transferred into the solvent phase and is extracted for removal. (U.S. Pat. Nos. 1,371,342, 2,345,097, etc.)

(3) Steam refining method:

Steam is blown in under vacuum to distill off the free fatty acid together with the steam. (Refer to "Yushi Kagaku Kogyo (Fat Chemical Industry), Kogyo Gijutsu Shinsho)".

(4) Excess addition method:

In addition to the catalytic amount sufficient for the interesterification, an alkali is added in an excess amount corresponding to the free fatty acid.

(5) Pre-esterification method:

The free fatty acid is first esterified using an acid catalyst and the interesterification of the fat is then conducted using an alkali catalyst. (Japanese Patent Publication No. 1,823/1960, Japanese Patent Laid-Open Publication No. 62,926,/1975, etc.) Among the conventional methods as mentioned above, the method (1) makes it possible to efficiently remove not only the free fatty acid, but also other impurities. However, this method requires after-treatment of the removed soap, only a low yield of the product is obtained and the cost is increased. In order to sufficiently lower the acid value (AV) and to remove free fatty acids, the method (2) requires a considerably large amount of a solvent. When methanol is used as the solvent in order to reduce the AV from about 10 down to 0.8, for example, methanol must be used in an amount of five times as much by weight as coconut oil. In addition, method (2) cannot substantially remove impurities such as polypeptides and phospholipids.

The method (3) requires relatively large equipment and involves the problem of treating the distillates. As mentioned above, the method (4) involves the problems of deterioration of the quality of the product and increase of the loss of the materials due to the emulsifying and solubilizing action of the resulting fatty acid soap. On the other hand, the method (5) can be relatively easily used on the industrial scale. It has so far been reported, however, that impurities such as polypeptides and phospholipids are hardly removed and so they remain in the fat, even though free fatty acids could be esterified. If such fat is subjected to the interesterification reaction, it is difficult to recover and refine glycerol which contains almost all the impurities, whereby the loss of glycerol increases, because the impurities are almost entirely distributed into the glycerol layer. Moreover, those impurities that remain in the oil will lower the catalytic hydrogenation reactivity of the resulting lower alcohol ester of the fatty acid.

SUMMARY OF THE INVENTION

The inventions of the present invention have therefore made intensive research to achieve a process for obtaining a high quality lower alcohol ester of a fatty acid and glycerol from an unrefined fat, with a high yield, by solving the above-mentioned defects of the conventional methods, and thus completed the present invention. In accordance with the present invention, there is provided a process for producing lower alcohol esters of fatty acids which comprises steps including:

(1) esterifying free fatty acids of unrefined fats with a lower alcohol in an amount larger than the amount soluble in the fats, in the presence of an acid catalyst, or esterifying free fatty acids of unrefined fats with a lower alcohol in the presence of an acid catalyst and then adding the lower alcohol in an amount larger than the amount soluble in the fats;

(2) separating the product mixture into the fat layer and the lower alcohol layer, so that the latter layer may be removed; and (3) effecting the interesterification reaction between the resulting refined fats and a lower alcohol with an alkali catalyst.

After the esterification of the free fatty acid using an acid catalyst and the separation of the alcohol layer in the above-mentioned process, the procedure comprising adding again the lower alcohol in an amount larger than its soluble amount in the fat, stirring, settling, separating and removing the alcohol layer, may be further repeated at least once, and the resulting refined fats and the lower alcohol are subjected to the interesterification reaction using an alkali catalyst to thereby give a lower alcohol ester of the fatty acid having a further improved quality.

The unrefined fats and oils used as raw materials in the present invention are vegetable oils such as coconut oil, palm oil, palm kernel oil, cotton seed oil and soybean oil, and animal oils and fats such as beef tallow, lard and fish oil. These fats and oils are not refined or not completely refined. Accordingly, they contain free fatty acids, polypeptides, phospholipids, and other impurities.

Examples of the lower alcohol to be used in the present invention are aliphatic monohydric alcohols of 1 to 3 carbon atoms. More specifically, there may be used methanol, ethanol and isopropanol. Of these, methanol is most preferred from the economic point of view.

The solubility of an alcohol in the fat depends on various conditions. In the case of methanol, the solubility is from 12 to 15% by weight in the fat at 50° C. Accordingly, in the present invention, methanol is added in an amount larger than this solubility. More specifically, it is preferred to add methanol in an amount of 20 to 30% by weight based on the weight of the fat. The esterification reaction may be carried out in a sealed system after adding a lower alcohol in excess. However, in order to remove water generated during the reaction, it is more preferred that methanol is charged in excess at the start of the reaction and then further methanol is blown into the reaction system at the same rate as that at which methanol is being distilled out.

The esterification of free fatty acids by the use of an acid catalyst is carried out at a temperature in the range of from 60° to 120° C. In order to restrain the interesterification reaction of the fat component, however, a low temperature ranging from 65° to 70° C. is more preferred. As the acid catalyst to be used for this purpose, sulfuric acid and para-toluene-sulfonic acid and the like may be used. Examples of the alkali catalyst for the interesterification reaction are caustic soda, caustic potash, sodium methoxide, potassium methoxide and the like.

The most characteristic feature of the process for producing lower alcohol esters of fatty acids in accordance with the present invention resides in the following points. It is different from the conventional, solvent extraction method which merely removes free fatty acids by means of the solubility difference and the pre-esterification method in which free fatty acids are esterified with a lower alcohol into fatty acid esters so as to reduce the acid value. According to the process of the present invention, not only free fatty acids in unrefined fats are esterified to reduce their acid value, but also simultaneously the fats are treated with an acid catalyst for the purpose of the esterification and impurities other than the free fatty acids, such as polypeptides and phospholipids, are dissolved in the lower alcohol layer which is present in excess or is later added, and thus removed from the fats. The removal of these impurities is difficult without the acid treatment of the fats.

In other words, in the conventional solvent extraction method, these impurities have poor solubility in a solvent and they are hardly removed from the fat as they are. In the process of the present invention, on the other hand, the impurities such as polypeptides and phospholipids are decomposed while the fatty acid is being esterified under the acidic condition of sulfuric acid and their solubility in a lower alcohol is increased. As the result, the effect of removing impurities is remarkably enhanced in the solvent extraction step. Moreover, as the unreacted free fatty acid is distributed also to the lower alcohol layer to a certain extent, so it is also advantageous for the removal of the impurities.

It is added that glycerol and a part of the oils are dissolved in the lower alcohol layer. It is seen, however, that very little glycerol is produced at a temperature of 65° to 70° C. at which the interesterification hardly proceeds. Almost all of the oils which are distributed in the lower alcohol layer can be recovered in a suitable manner.

After the removal of the alcohol layer separated at the end of the esterification, the lower alcohol is added to the fat in an amount larger than its soluble amount in the fat (preferably 10 to 30% by weight based on the weight the fat), stirred, settled, and subjected to a layer separation procedure so as to remove the excess lower alcohol. When the cycle of these steps is repeated, the fats are improved in their quality. It is possible to re-use the resulting alcohol layer of this procedure in the step of adding a lower alcohol to the starting fats.

Fats are obtained in such a manner and then interesterified with a lower alcohol in the presence of an alkali catalyst to produce lower alcohol esters of fatty acids. Since free fatty acids and water have been removed, it is possible to remarkably reduce the amount of an alkali catalyst to be used and simultaneously restrain saponification by-reaction and minimize the loss of the oil content. The product of this invention, lower alcohol esters of fatty acids, provide a remarkable improvement in the reduction rate at which it is catalytically reduced into high alcohol esters.

Furthermore, since the fatty acid ester obtained in this invention does not contain impurities that deteriorate the color of the product, the color of the product is extremely excellent. As to the by-produced glycerol, the recovery yield of glycerol is improved because the loss caused by incorporation of the fat and the resulting emulsion is minimized. It is thus possible to obtain glycerol itself which has a good quality and can be easily refined.

In accordance with the present invention, it is now possible to obtain a fatty acid ester and glycerol of extremely high quality from unrefined fats and oils containing various impurities by employing the process comprising esterification, layer separation, washing with lower alcohol, layer separation and interesterification.

Following examples are given to illustrate the present invention. The term "%" used in the examples is based on the weight.

EXAMPLE 1

A four-necked flask of a 2 l-capacity equipped with a stirrer, a thermometer, a methanol blowing port and a condenser for distillates is charged with 1,000 g of a raw coconut oil having an acid value of 7.7, 205 g of methanol and 1 g of 98% concentrated sulfuric acid. The mixture is heated, and after methanol starts reflux, further methanol is blown into the flask at a constant rate so as to keep the methanol in the flask in the same amount as the initially charged water and methanol. The esterification reaction is carried out for 3 hours at a temperature of 65° to 67° C. At 3 hours after the blowing of methanol started, the blowing is stopped and the reaction system is then cooled to 50° C. Thereafter, the stirring is also stopped and the reaction system is allowed to stand, whereupon the upper methanol layer and the lower fat layer separate in a volume ratio of about 1:10. After the methanol layer is removed, 205 g of methanol is further added to the fat layer, and the mixture is stirred at 50° C. to wash the fat layer with it. In the same way as above, the methanol layer is separated. The acid value is lowered down to 0.3 in this instance.

1.74 g of caustic soda as an alkali catalyst and 75.6 g of methanol are added to the resulting fat and subjected to the interesterification reaction at about 50° C. for about 1 hour. The reaction mixture is allowed to stand, and the lower glycerol layer is removed. Then 1.74 g of caustic soda and 15.6 g of methanol are added and subjected to the interesterification for about 30 minutes. The reaction mixture is again allowed to stand to separate and remove the glycerol layer. There is thus obtained a coconut fatty acid methyl ester.

For comparison, the esterification of the fatty acid is carried out in substantially the same manner as above, except that the blowing of methanol, subsequent separation and removal of the methanol layer and washing of the fat with methanol are not effected. Then, the interesterification reaction is similarly performed between the resulting fat and methanol in the presence of the alkali catalyst to give a coconut fatty acid methyl ester and crude glycerol (pre-esterification method).

Both methyl esters as obtained above are examined with respect to the colour, the hydrogenation rate constant where the ester is catalytically reduced into a corresponding higher alcohol and the fat content in the crude glycerol which is considered to indicate the loss of fats. Results are shown in Table 1.

Table 1

| | Process of this invention | Pre-esterification method |
|---|---|---|
| Color of methyl ester (APHA) | 150 | 200 |
| Hydrogenation rate constant* (1/min) | $8.4 \times 10^{-3}$ | $6.8 \times 10^{-3}$ |
| Fat content in glycerol (%) | 3.0 | 7.2 |

*Calculated from a saponification value when 60 minutes have passed after hydrogenation is performed with a Cu-Cr catalyst at a temperature of 250° C. and a hydrogen pressure of 150 Kg/cm².

EXAMPLE 2

To 1,000 g of a raw coconut oil having an acid value of 7.7 are added 180 g of the methanol layer recovered in Example 1 (composition: 84% of methanol, 15% of fat content and 1% of others), 50 g of methanol and 1 g of concentrated sulfuric acid, and then subjected to the same procedures as in Example 1.

The coconut fatty acid methyl ester has a color of APHA 150, and when hydrogenated under the same hydrogenation condition as in Example 1, the hydrogenation rate constant is $8.5 \times 10^{-3}$ (1/min), and the quality of the ester is good.

EXAMPLE 3

In the same way as in Example 1, 1 g of concentrated sulfuric acid is added to 1,000 g of a raw coconut oil having an acid value of 7.7 and methanol in a rate of 90 g/h is blown in at 65°–67° C. Water formed during the esterification is distilled off together with methanol. At 3 hours after the initiation of blowing of methanol, blowing is stopped and the reaction mixture is cooled to 50° C. After 200 g of methanol is added, the mixture is stirred for about 10 minutes, and then settled to separate layers. The resulting methanol layer is removed.

Thereafter, 102.5 g of methanol is added and stirred at 50° C. and settled to separate layers, and the resulting methanol layer is separated. This procedure is repeated twice. The resulting fat is subjected to the interesterification reaction with methanol in the presence of an alkali catalyst in the same way as in Example 1.

The methyl ester thus obtained is found by measurement to have good quality of a color of APHA 150 and a hydrogenation rate constant of $8.4 \times 10^{-3}$ (1/min).

The embodiments of the invention in which an exclusive and privilege property is claimed are defined as follows:

1. A process for producing lower alcohol esters of fatty acids from an unrefined fat containing impurities including free fatty acids, polypeptides and phospholipids, which comprises the steps of:
   (1) reacting the free fatty acids of said unrefined fat with a lower alcohol, in the presence of an acid catalyst, to esterify said free fatty acids, the amount of said lower alcohol present in the reaction mixture at the end of the esterification reaction being an amount greater than the amount of said lower alcohol that can be dissolved in said fat whereby, at the end of the esterification reaction, the reaction mixture contains a fat phase and a lower alcohol phase, said lower alcohol phase containing impurities dissolved therein;
   (2) then separating said reaction mixture into a fat layer and a lower alcohol layer, removing said lower alcohol layer and thereby obtaining refined fat;
   (3) then adding a lower alcohol and an alkali catalyst to said refined fat and effecting an interesterification reaction to form lower alcohol esters of the fatty acids in said refined fat, and then recovering said lower alcohol esters.

2. A process as claimed in claim 1, in which in step (1), the esterification of the free fatty acids is effected at 60° to 120° C.

3. A process as claimed in claim 1, in which said lower alcohol has from one to three carbon atoms.

4. A process as claimed in claim 1, in which said lower alcohol is methyl alcohol.

5. A process as claimed in claim 1, in which in step (1), the esterification of the free fatty acids is effected at 65° to 70° C.

6. A process as claimed in claim 1, in which in step (1) the amount of said lower alcohol present during the esterification reaction is greater than the amount of said lower alcohol that can be dissolved in said unrefined fat.

7. A process as claimed in claim 1, in which the step (1), after completion of the esterification reaction, an additional quantity of said lower alcohol is added to the reaction mixture so that the amount of said lower alcohol present in the reaction mixture is greater than the amount of said lower alcohol that can be dissolved in said unrefined fat.

8. A process as claimed in claim 1, in which after step (2) and prior to step (3), an additional quantity of said lower alcohol is admixed with said fat wherein said quantity is an amount greater than the amount of said lower alcohol that can be dissolved in said fat, then allowing the mixture thereby formed to stand to separate same into a fat layer and a lower alcohol layer, then removing said lower alcohol layer and using said fat layer in step (3).

9. A process as claimed in claim 8, in which said steps of admixing said additional quantity of said lower alcohol, allowing the mixture thereby formed to separate and then removing said lower alcohol layer, are repeated at least once, and the fat layer finally obtained is then used in step (3).

10. A process as claimed in claim 8, in which said lower alcohol has one to three carbon atoms.

11. A process as claimed in claim 8, in which said lower alcohol is methyl alcohol.

12. A process as claimed in claim 4, in which the amount of methanol used in step (1) is from 20 to 30% by weight, based on the weight of the fat.

13. A process as claimed in claim 1, in which in step (1) the amount of said lower alcohol present at the start of the esterification reaction is greater than the amount of said lower alcohol that can be dissolved in said unrefined fat, during the esterification reaction distilling out water and said lower alcohol and simultaneously blowing in an additional quantity of said lower alcohol at the same rate at which said lower alcohol is being distilled out of the reaction mixture.

* * * * *